(12) United States Patent
Savage (10) Patent No.: US 10,676,501 B2
(45) Date of Patent: *Jun. 9, 2020

(54) HYDROGEL MATERIALS INCORPORATING ELUTING CERAGENIN COMPOUND

(75) Inventor: Paul B. Savage, Mapleton, UT (US)

(73) Assignee: BRIGHAM YOUNG UNIVERSITY, Provo, UT (US)

(*) Notice: Subject to any disclaimer, the term of this patent is extended or adjusted under 35 U.S.C. 154(b) by 340 days.

This patent is subject to a terminal disclaimer.

(21) Appl. No.: 13/554,930

(22) Filed: Jul. 20, 2012

(65) Prior Publication Data

US 2013/0022651 A1 Jan. 24, 2013

Related U.S. Application Data

(60) Provisional application No. 61/572,714, filed on Jul. 20, 2011, provisional application No. 61/642,431, filed on May 3, 2012.

(51) Int. Cl.
*A61L 27/14* (2006.01)
*C07J 41/00* (2006.01)
(Continued)

(52) U.S. Cl.
CPC ........... *C07J 41/0055* (2013.01); *A61L 27/14* (2013.01); *A61L 27/18* (2013.01); *A61L 27/34* (2013.01); *A61L 27/52* (2013.01); *A61L 27/54* (2013.01); *A61L 29/04* (2013.01); *A61L 29/085* (2013.01); *A61L 29/145* (2013.01); *A61L 29/16* (2013.01); *A61L 31/04* (2013.01); *A61L 31/10* (2013.01); *A61L 31/145* (2013.01); *A61L 31/16* (2013.01); *C07C 211/00* (2013.01);
(Continued)

(58) Field of Classification Search
CPC .... A61L 2300/404; A61L 27/34; A61L 27/52; A61L 27/54; A61L 29/085; A61L 29/145; A61L 29/16; A61L 31/10; A61L 31/145; A61L 31/16; A61L 2300/208; A61L 2300/606; A61L 27/14; A61L 27/18; A61L 29/04; A61L 31/04; C07C 211/00; C07J 41/0055
See application file for complete search history.

(56) References Cited

U.S. PATENT DOCUMENTS 3,843,779 A 10/1974 Norfleet
4,248,236 A 2/1981 Linder
(Continued)

FOREIGN PATENT DOCUMENTS

CN 101378761 3/2009
CN 102145005 8/2011
(Continued)

OTHER PUBLICATIONS

Bucki et al. (Salivary mucins inhibit antibacterial activity of the cathelicidin-derived LL-37 peptide but not the cationic steroid CSA-13, Journal of Antimicrobial Chemotherapy (2008) 62: 329-335), 7 pages.*

(Continued)

*Primary Examiner* — Ernst V Arnold
(74) *Attorney, Agent, or Firm* — Workman Nydegger (57) ABSTRACT

A hydrogel polymer includes a ceragenin compound. The ceragenin compound has a hydrophobicity/hydrophilicity that produces a release rate in a range of 0.1-100 µg/ml for at least 3 days.

19 Claims, 7 Drawing Sheets

(51) Int. Cl.
| | |
|---|---|
| *A61L 27/52* | (2006.01) |
| *A61L 27/54* | (2006.01) |
| *A61L 31/14* | (2006.01) |
| *A61L 31/16* | (2006.01) |
| *A61L 27/34* | (2006.01) |
| *A61L 29/08* | (2006.01) |
| *A61L 29/14* | (2006.01) |
| *A61L 29/16* | (2006.01) |
| *A61L 31/10* | (2006.01) |
| *C07C 211/00* | (2006.01) |
| *A61L 27/18* | (2006.01) |
| *A61L 29/04* | (2006.01) |
| *A61L 31/04* | (2006.01) |

(52) U.S. Cl.
CPC ... *A61L 2300/208* (2013.01); *A61L 2300/404* (2013.01); *A61L 2300/606* (2013.01)

(56) References Cited

U.S. PATENT DOCUMENTS

| | | |
|---|---|---|
| 4,289,755 A | 9/1981 | Dhabhar |
| 4,296,206 A | 10/1981 | Simons |
| 4,473,988 A | 10/1984 | Scott |
| 4,661,341 A | 4/1987 | Benedict et al. |
| 4,723,950 A | 2/1988 | Lee |
| 4,765,855 A | 8/1988 | Geoffroy-Dechaume et al. |
| 4,842,593 A | 6/1989 | Jordan et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,352,682 A | 10/1994 | Sipos |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,687,714 A | 11/1997 | Kolobow |
| 5,721,359 A | 2/1998 | Dunn et al. |
| 5,763,430 A | 6/1998 | Zasloff |
| 6,117,332 A | 9/2000 | Hatch et al. |
| 6,217,896 B1* | 4/2001 | Benjamin ............. A61F 9/0017 424/420 |
| 6,228,393 B1 | 5/2001 | DiCosmo et al. |
| 6,329,488 B1 | 12/2001 | Terry et al. |
| 6,350,738 B1 | 2/2002 | Savage et al. |
| 6,486,148 B2 | 11/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,767,904 B2 | 7/2004 | Savage et al. |
| 6,773,717 B1 | 8/2004 | Winstrom |
| 6,803,066 B2 | 10/2004 | Traeder |
| 6,872,306 B2 | 3/2005 | Knapp et al. |
| 6,939,376 B2 | 9/2005 | Shulze et al. |
| 7,235,552 B1 | 6/2007 | Hesse et al. |
| 7,282,214 B2* | 10/2007 | Willcox et al. ............... 424/429 |
| 7,381,439 B2 | 6/2008 | Hilgren et al. |
| 7,598,234 B2 | 10/2009 | Savage et al. |
| 7,659,061 B2 | 2/2010 | Hendl et al. |
| 7,754,705 B2 | 7/2010 | Savage et al. |
| 7,854,941 B2 | 12/2010 | Urban et al. |
| 7,993,903 B2 | 8/2011 | Hayakawa et al. |
| 8,211,879 B2 | 7/2012 | Savage et al. |
| 8,529,681 B1 | 9/2013 | Hibbs et al. |
| 8,530,002 B1 | 9/2013 | Hibbs et al. |
| 8,623,416 B2 | 1/2014 | Zasloff et al. |
| 8,691,252 B2 | 4/2014 | Savage |
| 8,784,857 B2* | 7/2014 | Savage ............. A01N 45/00 424/400 |
| 8,787,857 B2 | 7/2014 | Savage |
| 8,932,614 B2* | 1/2015 | Savage ............. A61L 27/34 424/400 |
| 8,945,217 B2* | 2/2015 | Savage ............. A61L 27/34 623/11.11 |
| 8,975,310 B2* | 3/2015 | Savage ............. A61L 27/52 523/122 |
| 9,527,883 B2 | 12/2016 | Savage et al. |
| 9,533,063 B1* | 1/2017 | Savage ............. A01N 45/00 |
| 9,546,195 B2* | 1/2017 | Savage ............. A61L 27/52 |
| 2002/0091278 A1* | 7/2002 | Savage ............. C07J 41/0055 552/9 |
| 2003/0018306 A1 | 1/2003 | Bucay-Couto et al. |
| 2003/0099717 A1 | 5/2003 | Cabrera |
| 2003/0170354 A1 | 9/2003 | Beelman et al. |
| 2004/0009227 A1* | 1/2004 | Yao ............................. 424/486 |
| 2004/0011358 A1 | 1/2004 | Smaldone et al. |
| 2004/0018154 A1 | 1/2004 | Pan |
| 2004/0058974 A1 | 3/2004 | Courtney et al. |
| 2004/0071781 A1 | 4/2004 | Chattopadhyay et al. |
| 2004/0126409 A1 | 7/2004 | Wilcox et al. |
| 2004/0134292 A1 | 7/2004 | Roth |
| 2004/0170563 A1 | 9/2004 | Meade |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0053788 A1 | 3/2007 | Zhao |
| 2007/0077292 A1 | 4/2007 | Pinsky |
| 2007/0106393 A1 | 5/2007 | Miles et al. |
| 2007/0154554 A1 | 7/2007 | Burgermeister et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0124376 A1* | 5/2008 | Pruitt .................. A61K 9/0051 424/427 |
| 2008/0174035 A1* | 7/2008 | Winterton ................. 264/1.36 |
| 2008/0188819 A1* | 8/2008 | Kloke et al. ................. 604/304 |
| 2008/0279944 A1 | 11/2008 | Sawhney |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0099531 A1 | 4/2009 | Griesbach, III |
| 2009/0252781 A1 | 10/2009 | Sawhney et al. |
| 2009/0324517 A1 | 12/2009 | Kline |
| 2010/0022481 A1* | 1/2010 | Wang ................. A61K 31/6615 514/108 |
| 2010/0092398 A1 | 4/2010 | Reynolds |
| 2010/0209497 A1 | 8/2010 | Thornthwaite |
| 2010/0226884 A1 | 9/2010 | Chang et al. |
| 2010/0310478 A1 | 12/2010 | Fitzgerald et al. |
| 2010/0330086 A1 | 12/2010 | Savage et al. |
| 2011/0091376 A1 | 4/2011 | Savage et al. |
| 2011/0123624 A1 | 5/2011 | Zasloff |
| 2011/0135742 A1 | 6/2011 | Kim et al. |
| 2011/0171144 A1 | 7/2011 | Wang et al. |
| 2011/0230589 A1 | 9/2011 | Maggio et al. |
| 2012/0088733 A1 | 4/2012 | Kim et al. |
| 2012/0107382 A1 | 5/2012 | Savage |
| 2012/0128793 A1 | 5/2012 | Miller et al. |
| 2013/0004586 A1 | 1/2013 | Vachon |
| 2013/0053507 A1 | 2/2013 | Savage |
| 2013/0040265 A1 | 3/2013 | Park et al. |
| 2013/0137668 A1 | 5/2013 | Fein et al. |
| 2013/0236619 A1 | 9/2013 | Savage |
| 2013/0243823 A1 | 9/2013 | Genberg et al. |
| 2013/0243840 A1 | 9/2013 | Savage et al. |
| 2013/0243842 A1 | 9/2013 | Genberg et al. |
| 2013/0245760 A1 | 9/2013 | Savage et al. |
| 2013/0280312 A1 | 10/2013 | De Szalay |
| 2013/0280391 A1 | 10/2013 | Savage |
| 2014/0107090 A1 | 4/2014 | Beus et al. |
| 2014/0194401 A1 | 7/2014 | Genberg et al. |
| 2014/0219914 A1 | 8/2014 | Govindan et al. |
| 2014/0228905 A1 | 8/2014 | Bolea |
| 2014/0271761 A1 | 9/2014 | Savage et al. |
| 2014/0274913 A1 | 9/2014 | Savage et al. |
| 2014/0305461 A1 | 10/2014 | Pimenta et al. |
| 2014/0315873 A1 | 10/2014 | Beus et al. |

(56) References Cited

U.S. PATENT DOCUMENTS

| | | |
|---|---|---|
| 2014/0363780 A1 | 12/2014 | Vazquez et al. |
| 2014/0369941 A1 | 12/2014 | Vazquez et al. |
| 2015/0140063 A1 | 5/2015 | Savage |
| 2015/0203257 A1 | 7/2015 | Canegallo |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |
| 2016/0193232 A1 | 3/2016 | Beus et al. |
| 2016/0199390 A1 | 3/2016 | Beus et al. |
| 2016/0311850 A1 | 10/2016 | Savage et al. |
| 2016/0311851 A1 | 10/2016 | Savage et al. |
| 2017/0035677 A1 | 2/2017 | Vazquez et al. |
| 2017/0080128 A1 | 3/2017 | Genberg et al. |
| 2017/0137459 A1 | 5/2017 | Savage |
| 2017/0210776 A1 | 7/2017 | Savage |
| 2017/0232004 A1 | 8/2017 | Savage et al. |
| 2017/0258963 A1 | 9/2017 | Savage et al. |

FOREIGN PATENT DOCUMENTS

| | | |
|---|---|---|
| CN | 102172356 | 9/2011 |
| DE | 1037074 | 8/1958 |
| EP | 0341951 | 11/1989 |
| EP | 1208844 | 5/2002 |
| EP | 1219631 | 7/2002 |
| EP | 1250849 | 10/2002 |
| JP | 02014741 | 1/1990 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | WO 1993001829 | 2/1993 |
| WO | WO 1995024415 | 9/1995 |
| WO | WO9827106 | 6/1998 |
| WO | WO 1999044616 | 9/1999 |
| WO | WO 2000042058 | 7/2000 |
| WO | WO 2002014342 | 2/2002 |
| WO | WO2002067979 | 9/2002 |
| WO | WO 2003015757 | 2/2003 |
| WO | WO 03090799 | 11/2003 |
| WO | WO2004082588 | 9/2004 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | WO2008048340 | 4/2008 |
| WO | WO2008096149 | 8/2008 |
| WO | WO 2008038965 | 4/2009 |
| WO | WO2009049370 | 4/2009 |
| WO | WO 2009079066 | 6/2009 |
| WO | WO2009144708 | 12/2009 |
| WO | WO2010006192 | 1/2010 |
| WO | WO 2010036427 | 4/2010 |
| WO | WO 2010062562 | 6/2010 |
| WO | WO2011066260 | 6/2011 |
| WO | WO 2011109704 | 9/2011 |
| WO | WO 2012/061651 | 5/2012 |
| WO | WO 2013029055 | 2/2013 |
| WO | WO 2013029059 | 2/2013 |
| WO | WO2013040269 | 3/2013 |
| WO | WO2013131060 | 6/2013 |
| WO | WO2013/109236 | 7/2013 |
| WO | WO2013109236 | 7/2013 |
| WO | WO 2013167743 | 11/2013 |
| WO | WO 2014062960 | 4/2014 |
| WO | WO 2014151411 | 9/2014 |
| WO | WO2015058087 | 4/2015 |
| WO | WO2015200815 | 12/2015 |
| WO | WO2016172543 | 10/2016 |
| WO | WO2016186821 | 11/2016 |

OTHER PUBLICATIONS

Wu et al., Biodegradable hydrophobic-hydrophilic hybrid hydrogels: swelling behavior and controlled drug release, Journal of Biomaterials Science Polymer Edition (J. Biomater. Sci. Polymer Ed.) (2008) 19 (4): 411-429 (20 pages).*

Oxford Dictionaries (on-line) definition of Adsorb ([Retrieved from internet <URL: http://www.oxforddictionaries.com/us/definition/american_english/adsorb >] [Downloaded Mar. 10, 2015]).*

Lowe et al. (Effect of Hydrophobicity of a Drug on its Release from Hydrogels with Different Topological Structures, Journal of Polymer Science (1999) 73: 1031-1039) (9 pages).*

Sigma-Aldrich, Poly(ethylene-co-vinyl acetate), [Retrieved from internet <URL: http://www.sigmaaldrich.com/catalog/product/aldrich/340502?lang=en&region=US >], [Downloaded Jul. 22, 2016], excerpt in action.*

BASF, Pluronic® Block Copolymer NF Grades (Poloxamer NF Grades), Technical Bulletin (2004), 2 pg (Year: 2004).*

BASF, [Retrieved from internet <URL: https://worldaccount.basf.com/wa/NAFTA~en_US/Catalog/ChemicalsNAFTA/doc4/BASF/PRD/30085231/.pdf?asset_type=pi/pdf&language=EN&urn=urn:documentum:eCommerce_sol_EU:09007bb280022b53.pdf >] (Year: 2004).*

Chin et al. (Antimicrobial Activities of Ceragenins against Clinical Isolates of Resistant *Staphylococcus aureus*, Antimicrobial Agents and Chemotherapy (Apr. 2007) 51 (4): 1268-1273) (Year: 2007).*

Derakhshandeh et al. (Thermosensitive Pluronic® hydrogel: prolonged injectable formulation for drug abuse; Drug Design, Development and Therapy (2010), 4:255-262 (8 pages) (Year: 2010).*

Polat et al., In Vitro Amoebicidal Activity of a Ceragenin, Cationic Steroid Antibiotic-13, Against Acanthamoeba castellanii and Its Cytotoxic Potential, Journal of Ocular Pharmacology and Therapeutics (J Ocul Pharmacol Ther) (Feb. 2011), 27 (1): 1-5 (Year: 2011).*

Journal of Ocular Pharmacology and Therapeutics, vol. 27, Issue 1, Table of Contents (Mary Ann Liebert, Inc. publishers) [Retrieved from internet <URL: http://online.liebertpub.com/toc/jop/27/1 >], [Downloaded Dec. 1, 2017], 5 pages (Year: 2017).*

Ahmed, Hydrogel: Preparation, characterization, and applications: A review, Journal of Advanced Research (2015) 6: 105-121 (Year: 2015).*

P B Savage et al: "Thin Films Containing Ceragenins Prevent Biofilm Formation on Endotracheal Tubes", 9th International Federation of Infection Control Congress, Oct. 14, 2008 (Oct. 14, 2008), pp. 1-1, XP55016800, Santiago, Chile Retrieved from the Internet: URL:http://www.n8medical.com/PDF/EndotrachealTubePoster-IFIC.PDF[retrieved on Jan. 18, 2012].

PCT/US2012/047750, Oct. 5, 2012, International Search Report.

U.S. Appl. No. 14/288,126, filed May 27, 2014, Savage, et al.

Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.

K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.

Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.

Savage, et al., "Antibacterial Activities of Thin Films Containing Ceragenins", Microbial Surfaces: Structure, Interactions and Reactivity, ACS, May 30, 2008, pp. 65-78.

(56) References Cited

OTHER PUBLICATIONS

P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Alhanout K et al: "Squalamine as an example of a new potent antimicrobial agents class: a critical review.", Current Medicinal Chemistry 2010, vol. 17, No. 32, 2010, pp. 3909-3917.
U.S. Appl. No. 13/554,957, filed Apr. 1, 2014, Office Action.
U.S. Appl. No. 13/554,957, filed Aug. 1, 2014, Notice of Allowance.
U.S. Appl. No. 13/594,608, filed Jan. 30, 2014, Office Action.
U.S. Appl. No. 13/594,612, filed May 15, 2014, Office Action.
U.S. Appl. No. 13/615,324, filed Jan. 30, 2014, Office Action.
U.S. Appl. No. 13/783,007, filed Mar. 1, 2013, Savage, Paul B.
U.S. Appl. No. 14/339,342, filed Jul. 23, 2014, Vazquez, et al.
U.S. Appl. No. 14/341,304, filed Jul. 25, 2014, Savage, et al.
U.S. Appl. No. 14/515,858, filed Oct. 16, 2014, Savage, et al.
U.S. Appl. No. 14/398,094, filed Oct. 30, 2014, Savage, et al.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Paul B. Savage, et al: "Antibacterial Properties of cationic steroid antibiotics", FEMS Microbiology Letters, vol. 217, Nov. 2002, pp. 1-7.
Lai, et al., "Controlled Released of a Bactericidal Ceragenin-Polymer Conjugate", Sep. 227, 2006, p. 1, 46th Annual Interscience Conference on Antimicrobial Agents and Chemotherapy.
Li Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Ding, et al., "Origins of cell selectivity of cationic steroid antibiotics", Journal of American Chemical Society, Oct. 2004, pp. 13642-13648.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
International Search Report for PCT Application No. PCT/US2009/047485 dated Feb. 17, 2010.
International Search Report for PCT Application No. PCT/US2013/038090, dated Jul. 24, 2013.
Steeneveld, et al., "Cow-specific treatment of clinical mastitis: an economic approach", Journal of Dairy Science vol. 94, Jan. 2011, pp. 174-188
Qunying Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/o10062704/suppl file/o10062704 sl.pdf.

Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Chin et al, "Antimicrobial Activities of Ceragenins against Clinicial Isolates of Resistant *Staphylococcus aureas*.", Antimcirobial Agents and Chemotherapy, vol. 51, No. 4, Apr. 2007, p. 1268-1273.
Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
International Search Report for PCT Application No. PCT/US2011/059225 dated Jan. 31, 2012.
International Search Report for PCT Application No. PCT/US2012/055248 dated Feb. 14, 2013.
International Search Report for PCT Application No. PCT/US2012/055244 dated Dec. 5, 2012.
U.S. Appl. No. 13/288,902, filed Jun. 21, 2012, Restriction Requirement.
U.S. Appl. No. 13/288,902, filed Nov. 7, 2012, Office Action.
U.S. Appl. No. 13/000,010, filed Dec. 4, 2012, Restriction Requirement.
U.S. Appl. No. 13/288,892, filed Dec. 10, 2012, Restriction Requirement.
U.S. Appl. No. 13/288,892, filed May 9, 2013, Office Action.
U.S. Appl. No. 13/288,902, filed Aug. 9, 2013, Notice of Allowance.
U.S. Appl. No. 13/288,892, filed Nov. 29, 2013, Notice of Allowance.
U.S. Appl. No. 14/056,122, filed Sep. 3, 2014, Office Action.
U.S. Appl. No. 13/783,131, filed Oct. 23, 2014, Office Action.
U.S. Appl. No. 13/783,007, filed Mar. 1, 2013, Savage.
U.S. Appl. No. 14/364,283, filed Jul. 29, 2014, Vazquez et al.
U.S. Appl. No. 14/602,499, filed Jan. 22, 2015, Savage.
U.S. Appl. No. 14/602,071, filed Jan. 21, 2015, Savage.
U.S. Appl. No. 14/624,200, filed Feb. 17, 2015, Savage.
U.S. Appl. No. 14/642,905, filed Mar. 10, 2015, Beus et al.
U.S. Appl. No. 14/644,946, filed Mar. 11, 2015, Beaus et al.
U.S. Appl. No. 14/645,040, filed Mar. 11, 2015, Savage et al.
U.S. Appl. No. 13/615,244, filed Sep. 13, 2012, Office Action dated Jan. 16, 2015.
U.S. Appl. No. 14/257,776, filed Apr. 21, 2014, Restriction Requirement dated Jan. 22, 2015.
U.S. Appl. No. 14/364,283, filed Jul. 29, 2014, Office Action dated Feb. 11, 2015.
U.S. Appl. No. 14/339,342, filed Jul. 23, 2014, Office Action dated Mar. 5, 2015.
U.S. Appl. No. 13/783,007, filed Mar. 1, 2013, Restriction Requirement dated Mar. 31, 2015.
U.S. Appl. No. 13/000,010, filed Dec. 17, 2010, Office Action dated Apr. 14, 2015.
U.S. Appl. No. 14/257,776, filed Apr. 21, 2014, Office Action dated Apr. 16, 2015.
U.S. Appl. No. 13/841,549, filed Mar. 15, 2013, Office Action dated Apr. 23, 2015.
U.S. Appl. No. 14/694,028, filed Apr. 23, 2015, Beus et al.
U.S. Appl. No. 14/750,928, filed Jun. 25, 2015, Genberg et al.
U.S. Appl. No. 14/830,356, filed Aug. 19, 2015, Savage.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/866,213, filed Sep. 25, 2015, Savage.
U.S. Appl. No. 14/873,013, filed Oct. 1, 2015, Savage et al.
U.S. Appl. No. 14/875,953, filed Oct. 6, 2015, Savage.
U.S. Appl. No. 14/926,738, filed Oct. 29, 2015, Vazquez et al.
Berge et al., "Pharmaceutical Salts", Journal of Pharmaceutical Sciences, Jan. 1977, vol. 66, No. 1, pp. 1-19.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.

(56) References Cited

OTHER PUBLICATIONS

Clara et al., "Preclinical evaluation of magainin-A as a contraceptive antimicrobial agent", Fertility and Sterility 81 (5), pp. 1357-1365, 2004.
International Search Report for PCT Application No. PCT/US2014/034986 dated Aug. 28, 2014.
International Search Report for PCT Application No. PCT/US2013/065510, dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Suzuki et al., "Molecular Genetics of Plant Sterol Backbone Synthesis", 2007; Lipids; 42: 47-54.
Van Den Bogaard et al., "Antibiotic Usage in Animals: Impact on Bacterial Resistance and Public Health"; 1999; Drugs; 58 (4): 589-607.
Zanger et al., "Structure-Activity Relationship and Drug Design", Remington's Pharmaceutical Sciences, Chapter 27, 16th Edition, 1980, pp. 420-425.
Brown, "Bioisosteres in Medicinal Chemistry, First Edition", edited by Nathan Brown, 2012, Ch. 2 Classical Bioisosteres, pp. 1-52.
Bush, "Staphylococcal Infections", Merck Manuals Professional Edition, http://www.merckmanuals.com/professional/infectious-diseases/gram-positive-cocci/staphylococcal-infections.
De Cuyper et al., "Surface functionalization of magnetoliposomes in view of improving iron oxide-based magnetic resonance imaging contrast agents: Anchoring of gadolinium ions to a lipophilic chelate", 2007 Anal. Biochem. 367: 266-273. Published online May 10, 2007.
Dennison et al., "Anticancer α-Helical Peptides and Structure/Function Relationships Underpinning their Interactions with Tumor Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Fichna et al., "Synthesis of Target-Specific Radiolabeled Peptides for Diagnostic Imaging", Bioconjugate Chem., 2003, 14, 3-17, American Chemical Society.
Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Li et al., "Incremental conversion of Outer-Membrane Permeabilizers into Potent Antibiotics for Gram-Negative Bacteria", J. Am. Chem. Soc. 1999, 121, 931-940.
Massoud et al., "Molecular imaging in living subjects: seeing fundamental biological processes in a new light", Genes & Development 17: 545-580 2003, Cold Spring Harbor Laboratory Press.
Muñoz-Juárez et al., "Wide-Lumen Stapled Anastomosis vs. Conventional End-to-End Anastomosis in the Treatment of Crohn's Disease", Dis Colon Rectum 2001; 44: No. 1, 20-26).
Papo et al., "Host peptides as new weapons in cancer treatment", CMLS Cell. Mol. Life Sci. 62 (2005), 784-790.
Roohi et al., Prepration, quality control and biological evaluation of 99m-Tc-labelled cationic steroid antibiotic (CSA-13), Radiochim. Acta 197, 57-62 (2009).
Schmidmaier et al., "Local Application of Growth Factors (Insulin-Like Growth Factor-1 and Transforming Growth Factor-β1) From a Biodegradable Poly(D, L-lactide) Coating of Osteosynthetic Implants Accelerates Fracture Healing in Rats", Bone vol. 28 No. 4, Apr. 2001.
Winter et al., "Improved paragmentic chelate for molecular imaging with MRI", 2005 J. Magn. Magn. Mater. 293: 540-545.
U.S. Appl. No. 15/934,534, filed Mar. 23, 2018, Savage, Paul B.
U.S. Appl. No. 15/895,848, filed Feb. 13, 2018, Genberg, et al.
U.S. Appl. No. 15/926,534, filed Mar. 20, 2018, Savage.
U.S. Appl. No. 15/926,577, filed Mar. 20, 2018, Savage et al.
U.S. Appl. No. 16/184,211, filed Nov. 8, 2018, Savage.
Belikov V.G., Pharmaceutical Chemistry, M., Higher School, 1993, p. 43-47, (Translation attached.).
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
International Search Report for PCT Application No. PCT/US2018/023566 dated Mar. 21, 2018.
Piktel et al. Sporicidal Activity of Ceragenin CSA-13 Against Bacillus Subtillis, Scientific Reports, vol. 7, Mar. 15, 2017 [retrieved on Apr. 24, 2018. Retreived from the internet: <URL: https://www.nature.com/articles/srep44452.pdf> Entire Document.
Welling et al., "Radiochemical and biological characteristics of 99m-Tc-UBI 29-41 for imaging of bacterial infections", Nuclear Medicine and Biology 29 (2002) 413-422.
Uncategorized: CSA Biotechnologies LLC, Apr. 5, 2011.
"Martindale: the complete drug reference, Cetrimide; Cetylpyridinium chloride ED-PARFITT K", Jan. 1, 2000, pp. 1105-1106.
Barton, Journal of Clinical Investigation, vol. 118, No. 2, Feb. 2008, Review Series, pp. 413-420.
Feng, Theses Brigham Young University, BYU Scholars Archive, dated Dec. 19, 2011, 190 pg.
Chen et al, J Drug Target, Dec. 2012; 20(10):856-63, 892.
Ogata et al. Intramammary application of ozone therapy to acute clinical mastitis in dairy cows. J. Vet. Med. Sci. 62(7): 681-686, 2000.
De Haas et al. Associations between pathogen-specific cases of clinical mastitis and somatic cell count patterns. J. Dairy Sci. 87: 95-105, (2004).
Weijian Ye et al "Synthesis and antibacterial activity of new long-chain-alkyl bile acid-based amphiphiles", Bioorganic Chemistry, vol. 51, Aug. 19, 2013, pp. 1-7, XP55513451, US ISSN: 0045-2068, DOI:10.1013/j.bioorg.2013.08.003.
"Quaternary Ammoniuim Compounds", Van Nostrand's Scientific Encyclopedia, Jan. 1, 2006, John Wiley & Sons, Inc., ( 3 pages).
Opsenica D, et al., "Cholic Acid Derivatives as 1,2,4,5-Tetraoxane Carriers: Structure and Antimalarial and Antiproliferative Activity", J. Med Chem. Aug. 2000, (Abs. only).
Valkonen, et al., "Bile acid amidoalcohols: simple organogelators", Biosens Bioelectron, Dec. 2004, (Abs. only).
Deepak B. Salunke et al., "Amino Functionalized Novel Cholic Acid Derivatives Induce HIV-1 Replication and Syncytia Formation in T Cells", J. Med. Chem. 2006, (4 pages).
Ding, et al., "Correlation of the Antibacerial Activities of Cationic Peptid Antibiotics and Cationic Steroid Antibiotics", J. Med. Chem., vo. 45, pp. 663-669 (Year: 2002).
Kuroda, et al., "Ceragenin CSA-13 induces cell cycle arrest and antiproliferative effects in wild-type and p52 null mutant HCT116 colon cancer cells", Preclinical Report, Wolters Kluwer Health 2013.

\* cited by examiner

CSA - 13
CLogP: 5.228

CSA - 44
CLogP: 6.351

CSA - 90
CLogP: 6.0858

CSA - 131
CLogP: 7.344

*FIG. 1*

CSA - 132
CLogP: 10.518

CSA - 133
CLogP: 17.7238

CSA - 134
CLogP: 8.402

CSA - 135
CLogP: 9.46

*FIG. 1 (continued)*

CSA - 136
CLogP: 6.286

CSA - 137
CLogP: 6.815

CSA - 138
CLogP: 7.873

CSA-139

FIG. 1 (continued)

CSA - 142
CLogP: 5.293

CSA - 144
CLogP: 7.409

CSA - 145
CLogP: 6.88

CSA - 146
CLogP: 5.822

HYDROGEL MATERIALS INCORPORATING ELUTING CERAGENIN COMPOUND

CROSS-REFERENCE TO RELATED APPLICATIONS

This application claims the benefit of U.S. Provisional application Nos. 61/572,714 filed Jul. 20, 2011, titled "Ceragenin-Containing Hydrogels For Prevention of Bacterial Biofilm Formation" and 61/642,431, filed May 3, 2012, titled Hydrogel Materials Incorporating Eluting Ceragenin Compound," both of which are hereby incorporated herein by reference.

BACKGROUND OF THE INVENTION

1. The Field of the Invention

The present invention relates to hydrogel materials. The materials include a hydrogel polymer that incorporates ceragenin compound that controllably elute from the hydrogel polymer. The hydrogel materials may be formed into a contact lens.

2. The Relevant Technology

A hydrogel polymer is a polymer that can absorb and retain extremely large amounts of a liquid relative to its own mass. In deionized and distilled water a hydrogel polymer may absorb 500 times its weight (from 30-60 times its own volume). The ability of a hydrogel polymer to absorb water depends on the ionic concentration of the aqueous solution being absorbed. Saline solutions are less absorbed than distilled water. For example, a saline solution of 0.9% is absorbed by a hydrogel polymer on the order of 50 times the polymer's weight.

The total absorbency and swelling capacity are controlled by the type and degree of cross-linkers used to make the polymer. Hydrogel polymers are commonly made by polymerizing acrylic acid blended with sodium hydroxide in the presence of an initiator to form a poly-acrylic acid sodium salt (sometimes referred to as sodium polyacrylate).

BRIEF SUMMARY

The present invention relates to hydrogel materials that include a hydrogel polymer that controllably elutes a ceragenin compound from the hydrogel polymer over time. The controlled elution of the ceragenin can occur over days, weeks, or months at a release rate that is within a desired range for making the hydrogel material anti-microbial while still maintaining the desired properties of the hydrogel material. In one embodiment, the hydrogel may be incorporated into a medical device or form a coating thereon. For example, the hydrogel may be coated on an implantable medical device or formulated into a contact lens.

Ceragenin compounds are anti-microbial compounds that have cationic groups attached to a sterol backbone. The compounds mimic the three-dimensional structure of naturally occurring anti-microbial peptides and provide a natural mechanism of killing microbes.

According to one embodiment of the invention, a ceragenin compound is incorporated into a hydrogel material and the hydrophobicity/hydrophilicity of the hydrogel polymer and the ceragenin compound are selected to cause the ceragenin compound to non-covalently bond to the hydrogel polymer. The non-covalent bonding prevents the ceragenin compound from being released all at once when placed in water or another fluid medium. The non-covalent bonding allows the ceragenin compound to be released over time. In one embodiment, the non-covalent bonding yields a release rate of 0.1-100 µg/ml, 0.5-50 µg/ml, or 1-10 µg/ml at three days, one week, or one month and/or over a period of at least 3 days, one week, or one month.

Surprisingly and unexpectedly, it has been found that by non-covalently bonding the ceragenin to a hydrogel using hydrophobic/hydrophilic interactions, the ceragenin compound can preferentially elute in the presence of microbes. In other words, the ceragenin can be "consumed" or removed from the hydrogel at a rate that is faster than the elution rate without the presence of the microbes. The data surprisingly show that microbes entering the hydrogel are attracted to the ceragenin compound. Because the ceragenins are non-covalently bonded, the microbes do not become immobilized on the surface of the hydrogel polymer, which is believed to avoid the buildup of biofilm and allow the continued elution of ceragenin and/or kill of microbes. The increased rate of elution or consumption of the ceragenin in the presence of microbes is a highly desirable and surprising and unexpected result.

The ceragenin compound can be incorporated into the hydrogel polymer by (i) polymerizing the hydrogel polymer in the presence of the ceragenin compound, (ii) intimately mixing the ceragenin with the hydrogel polymer (e.g., in dry form), and/or (iii) imbuing the hydrogel polymer with the ceragenin compound dissolved in a solvent.

In addition, it has been found that the ceragenins as used in the present invention surprisingly kill harmful microbes preferentially over normal flora, which means that the ceragenins can be used at lower concentrations compared to other antimicrobials while achieving the same or better effectiveness. This feature avoids many of the deleterious effects of prior art antimicrobials, many of which tend to kill the "good microbes."

The ceragenin eluting hydrogels can be incorporated into or formed into medical devices such as medical devices to be implanted into a human or other animal. For example, the hydrogels can be coated on a medical device. In another embodiment, the hydrogels incorporating ceragenin eluting compounds can be formed into ophthalmic products such as contact lenses. The hydrogel materials are particularly advantageous for medical devices due to the controlled release over periods of time that are needed for medical treatment or for maintaining shelf life of products such as ophthalmic products. For example, the ophthalmic products can controllably release ceragenin compound in a concentration sufficient to meet regulatory requirements for maximum bacterial loads over weeks or even months in a saline solution having the contact lens submersed therein.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Ceragenins

Ceragenin compounds, also referred to herein as cationic steroidal anti microbial compounds (CSA), are synthetically produced small molecule chemical compounds that include a sterol backbone having various charged groups (e.g., amine and cationic groups) attached to the backbone. The backbone can be used to orient the amine or guanidine groups on one face, or plane, of the sterol backbone. For example, a scheme showing a compound having primary amino groups on one face, or plane, of a backbone is shown below in Scheme I:

Scheme I

Ceragenins are cationic and amphiphilic, based upon the functional groups attached to the backbone. They are facially amphiphilic with a hydrophobic face and a polycationic face. Without wishing to be bound to any particular theory, the anti-microbial ceragenin compounds described herein act as anti-microbial agents (e.g., anti-bacterials, anti-fungals, and anti-virals). It is believed, for example, that the anti-microbial ceragenin compounds described herein act as anti-bacterials by binding to the outer cellular membrane of bacteria and other microbes and inserting into the cell membrane forming a pore that allows the leakage of ions that are critical to the microbe's survival and leading to the death of the affected microbe. In addition, the anti-microbial ceragenin compound described herein may also act to sensitize bacteria to other antibiotics. For example, at concentrations of the anti-microbial ceragenin compounds below the corresponding minimum bacteriostatic concentration, the ceragenins cause bacteria to become more susceptible to other antibiotics by increasing the permeability of the outer membrane of the bacteria.

Figure 1:
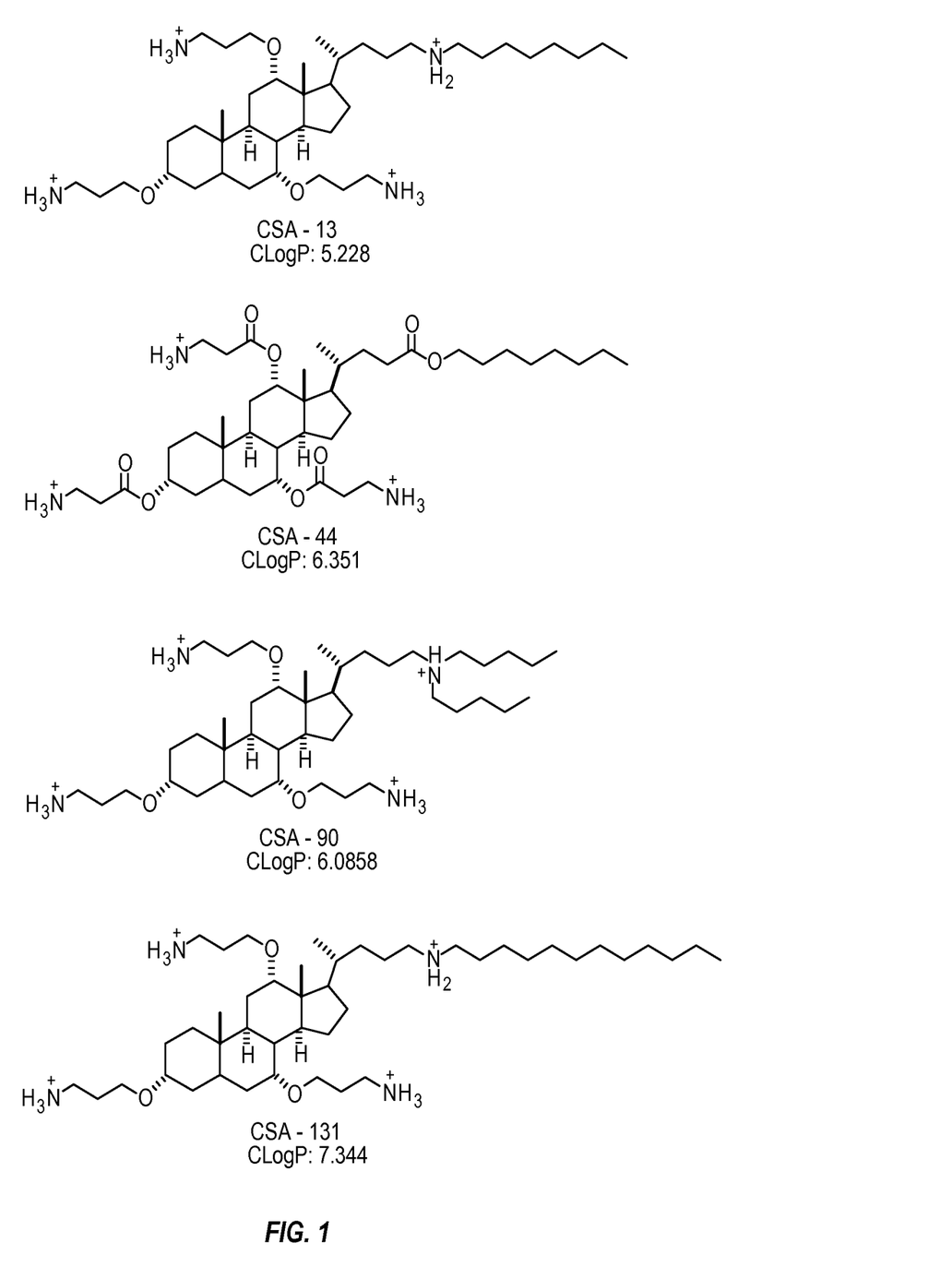
FIG. 1 illustrates example ceragenin compounds.

The charged groups are responsible for disrupting the bacterial cellular membrane, and without the charged groups, the ceragenin compound cannot disrupt the membrane to cause cell death or sensitization. A number of examples of ceragenin compounds of Formula I that can be incorporated into the composite materials described herein are illustrated in FIG. 1.

II. Hydrogel Polymers

The hydrogel polymers useful in the present invention include any hydrogel suitable for use in products where there is a need to minimize microbial load. For example, the hydrogels of the present invention may be hydrogels useful in making medical devices, medical device coatings, tissue scaffolds, wound dressings, contact lenses.

Examples of suitable hydrogel polymers include, but are not limited to, polyvinyl alcohol, sodium polyacrylate, acrylate polymers, polyethylene oxide, poly(2-acrylamido-2-methyl-1-propanesulfonic acid) (polyAMP S), polyvinylpyrrolidone, polyacrylamide, silicone, agarose, methylcellulose, hyaluronan, hydrolyzed polyacrylicnitrile, combinations of these. The hydrogels may be copolymers. The copolymers may include hydrophobic and hydrophilic units.

In one embodiment, the hydrogel is suitable for manufacturing a contact lens. Hydrophilic contact lenses can be formed from cross-linked polymers based on hydrophilic derivatives of acrylic or methacrylic acid, hydrophilic vinylic monomers such as vinylpyrrolidone, and the like. The hydrogels preferably include hydrophobic regions made from blocks or monomers that are hydrophobic.

An example of a suitable contact lens hydrogel is disclosed in U.S. Pat. No. 8,011,784, which is incorporated herein by reference.

The hydrogel polymers may be formed into a contact lens having a shape and structure suitable for correcting vision. Those skilled in the art are familiar with the shapes and structures of hydrogel polymers that can provide correction for vision. Other devices that can be formed from the hydrogels include wound healing devices such as tissue scaffolds and wound dressing.

III. Eluting Ceragenin Compounds

The ceragenin compound is selected in combination with the hydrogel polymer to non-covalently bond to the hydrogel polymer such that over time the ceragenin is released from the hydrogel in the presence of a solvent such as water or saline and preferably preferentially released or consumed in the presence of microbes.

Those skilled in the art will recognize that the hydrophobicity/hydrophilicity needed to achieve the desired bonding will depend on the type of hydrogel polymer being paired with the particular ceragenin compound. Because ceragenins have a sterol backbone, which can provide a high degree of hydrophobicity, in some embodiments it may be preferred to use a hydrogel that includes hydrophobic regions (e.g., hydrophobic blocks or monomers). The ceragenin compounds may have moieties that impart the desired amount of hydrophobicity to non-covalently bond with the hydrophobic regions of the hydrogel polymers. In one embodiment the ceragenin compound may have a pendant chain to the sterol backbone with a hydrocarbon chain of at least 9 carbons.

The ceragenin compound may have a structure as shown in Formula I:

Formula I where rings A, B, C, and D form a fused ring system and at least one of the R groups on 2 or 3 of the 4 four fused rings has a cationic group. The other R groups on FIG. 1 can have a variety of different functionalities, thus providing the ceragenin compound with the desired properties for eluting from a hydrogel.

In a preferred embodiment, p=1 and q=0 and at least $R_3$, $R_7$, and $R_{12}$ independently include a cationic group attached to the fused ring system and $R_{17}$ is a hydrophobic substituent that includes a hydrophobic group selected to give the ceragenin compound its desired hydrophobic/hydrophilic characteristics, which allows the ceragenin compound to non-covalently bond to the hydrogel polymer and elute out over time and/or be selectively exposed to microbes. The $R_{17}$ substituent may be hydrophobic but still include one or more heteroatoms (O or N) by having sufficient number of carbon atoms attached thereto to form a hydrophobic group. The hydrophobic group may be branched, substituted, or unsubstituted and the branching may occur at the heteroatom (e.g., dialkyl amines). The hydrophobic substituent is preferably attached at $R_{17}$ when q=0 and $R_{18}$ when q=1, but may be attached at other locations on the D ring or on R groups at locations on rings A, B, or C of Formula I. Where a hydrophobic substituent has a hydrophobic group attached to a heteroatom of an alkyl group, the hydrophobic group may have from 1-20 carbons, preferably 8, 9, 10, 11, 12, or more carbons and 20, 18, 16 or fewer carbons or within a range thereof. The hydrophobic group may also include a hydrophobic moiety such as trimethylsilane. The hydrophobic group may include one or more alkyl groups each having 4 or more, 6 or more, 8 or more, 10 or more or 12 or more carbons. The hydrophobic group can be attached to the sterol structure by an alkyl group linking to the heteroatom. The linkage may be an ester, an ether, an amine, or an amide. Ester linkages are preferred where hydrolysis is desired and/or no charge is desired to impart greater hydrophobicity. There the heteroatom includes an amine, the hydrophobic group is preferably a dialkyl. Examples of a suitable hydrophobic substituents having a hydrophobic group as described herein are C13-alkylamino-C5-alkyl and di-(C1-C20) alkylamino-(C1-C10)-alkyl, which can be covalently bonded to the D ring at R17 or R18 (Formula I).

A number of examples of compounds of Formula I that may be used in the embodiments described herein are illustrated in FIG. 1. Suitable examples of ceragenins useful in producing a composition that will elute from a hydrogel include, but are not limited to, CSA-13, CSA-131, CSA-132, CSA-133, CSA-134, CSA-135, CSA-137, and CSA-138. These compounds can be advantageous for their relatively high hydrophobicity. Examples of CSA's with shorter chain hydrocarbons on $R_{17}$ include, but are not limited to CSA-136, CSA-142, CSA-146, CSA-90, and CSA 44, which are also shown in FIG. 1.

With reference again to Formula I, more specifically, each of fused rings A, B, C, and D is independently saturated, or is fully or partially unsaturated, provided that at least two of A, B, C, and D are saturated, wherein rings A, B, C, and D form a ring system; each of m, n, p, and q is independently 0 or 1; each of $R_1$ through $R_4$, $R_6$, $R_7$, $R_{11}$, $R_{12}$, $R_{15}$, $R_{16}$, and $R_{18}$ is independently selected from the group consisting of hydrogen, hydroxyl, a substituted or unsubstituted $(C_1-C_{10})$ alkyl, $(C_1-C_{10})$ hydroxyalkyl, $(C_1-C_{10})$ alkyloxy-$(C_1-C_{10})$ alkyl, $(C_1-C_{10})$ alkyl carboxy-$(C_1-C_{10})$ alkyl, $(C_1-C_{10})$ alkylamino-$(C_1-C_{10})$ alkyl, $(C_1-C_{10})$ alkylamino-$(C_1-C_{10})$ alkylamino, $(C_1-C_{10})$ alkylamino-$(C_1-C_{10})$ alkylamino-$(C_1-C_{10})$ alkylamino, a substituted or unsubstituted $(C_1-C_{10})$ aminoalkyl, a substituted or unsubstituted aryl, a substituted or unsubstituted arylamino-$(C_1-C_{10})$ alkyl, $(C_1-C_{10})$ haloalkyl, $C_2-C_6$ alkenyl, $C_2-C_6$ alkynyl, oxo, a linking group attached to a second steroid, a substituted or unsubstituted $(C_1-C_{10})$ aminoalkyloxy, a substituted or unsubstituted $(C_1-C_{10})$ aminoalkyloxy-$(C_1-C_{10})$ alkyl, a substituted or unsubstituted $(C_1-C_{10})$ aminoalkylcarboxy, a substituted or unsubstituted $(C_1-C_{10})$ aminoalkylaminocarbonyl, a substituted or unsubstituted $(C_1-C_{10})$ aminoalkylcarboxamido, $H_2N$—HC$(Q_5)$-C(0)-0-, $H_2N$—HC$(Q_5)$-C(0)-N(H)—, $(C_1-C_{10})$ azidoalkyloxy, $(C_1-C_{10})$ cyanoalkyloxy, P.G. —HN—HC$(Q_5)$-C(0)-0-, $(C_1-C_{10})$ guanidinoalkyloxy, $(C_1-C_{10})$ quaternaryammoniumalkylcarboxy, and $(C_1-C_{10})$ guanidinoalkyl carboxy, where $Q_5$ is a side chain of any amino acid (including a side chain of glycine, i.e., H), P.G. is an amino protecting group, and each of $R_5$, $R_8$, $R_9$, $R_{10}$, $R_{13}$, and $R_{14}$ is independently deleted when one of fused rings A, B, C, or D is unsaturated so as to complete the valency of the carbon atom at that site, or selected from the group consisting of hydrogen, hydroxyl, a substituted or unsubstituted $(C_1-C_{10})$ alkyl, $(C_1-C_{10})$ hydroxyalkyl, $(C_1-C_{10})$ alkyloxy-$(C_1-C_{10})$ alkyl, a substituted or unsubstituted $(C_1-C_{10})$ aminoalkyl, a substituted or unsubstituted aryl, $(C_1-C_{10})$ haloalkyl, $C_2-C_6$ alkenyl, $C_2-C_6$ alkynyl, oxo, a linking group attached to a second steroid, a substituted or unsubstituted $(C_1-C_{10})$ aminoalkyloxy, a substituted or unsubstituted $(C_1-C_{10})$ aminoalkylcarboxy, a substituted or unsubstituted $(C_1-C_{10})$ aminoalkylaminocarbonyl, $H_2N$—HC$(Q_5)$-C(0)-0-, $H_2N$—HC$(Q_5)$-C(0)-N(H)—, $(C_1-C_{10})$ azidoalkyloxy, $(C_1-C_{10})$ cyanoalkyloxy, P.G. —HN—HC$(Q_5)$-C(0)-0-, $(C_1-C_{10})$ guanidinoalkyloxy, and $(C_1-C_{10})$ guanidinoalkylcarboxy, where Q5 is a side chain of any amino acid, PG. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted $(C_1-C_{10})$ aminoalkyl, a substituted or unsubstituted $(C_1-C_{10})$ aminoalkyloxy, $(C_1-C_{10})$ alkylcarboxy-$(C_1-C_{10})$ alkyl, $(C_1-C_{10})$ alkylamino-$(C_1-C_{10})$ alkylamino, $(C_1-C_{10})$ alkylamino-$(C_1-C_{10})$ alkylamino $(C_1-C_{10})$ alkylamino, a substituted or unsubstituted $(C_1-C_{10})$ aminoalkylcarboxy, a substituted or unsubstituted arylamino $(C_1-C_{10})$ alkyl, a substituted or unsubstituted $(C_1-C_{10})$ aminoalkyloxy $(C_1-C_{10})$ aminoalkylaminocarbonyl, a substituted or unsubstituted $(C_1-C_{10})$ aminoalkylaminocarbonyl, a substituted or unsubstituted $(C_1-C_{10})$ aminoalkylcarboxyamido, a $(C_1-C_{10})$ quaternaryammonium alkylcarboxy, $H_2N$—HC$(Q_5)$-C(0)-0, $H_2N$—HC$(Q_5)$-C(0)—N(H)—, $(C_1-C_{10})$ azidoalkyloxy, $(C_1-C_{10})$ cyanoalkyloxy, P.G. —HN—HC(Q5)-C(0)-0-, $(C_1-C_{10})$ guanidinoalkyloxy, and a $(C_1-C_{10})$ guanidinoalkylcarboxy; or a pharmaceutically acceptable salt thereof. Additional examples of specific CSA compounds are disclosed in Applicant's copending U.S. application Ser. No. 13/288,902 Filed Nov. 3, 2012, which is incorporated herein by reference.

A "ring" as used herein can be heterocyclic or carbocyclic. The term "saturated" used herein refers to the fused ring of Formula I having each atom in the fused ring either hydrogenated or substituted such that the valency of each atom is filled. The term "unsaturated" used herein refers to the fused ring of Formula I where the valency of each atom of the fused ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$; $R_8$ and $R_{10}$; and $R_{13}$ and $R_{14}$.

The term "unsubstituted" used herein refers to a moiety having each atom hydrogenated such that the valency of each atom is filled.

The term "halo" used herein refers to a halogen atom such as fluorine, chlorine, bromine, or iodine.

Examples of amino acid side chains include but are not limited to H (glycine), methyl (alanine), —$CH_2$—(C=O)-$NH_2$ (asparagine), —$CH_2$—SH (cysteine), and —CH(OH)—$CH_3$ (threonine).

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. Substituted alkyl groups may have one, two, three or more substituents, which may be the same or different, each replacing a hydrogen atom. Substituents are halogen (e.g., F, Cl, Br, and I), hydroxyl, protected hydroxyl, amino, protected amino, carboxy, protected carboxy, cyan, methylsulfonylamino, alkoxy, acyloxy, nitro, and lower haloalkyl.

The term "substituted" used herein refers to moieties having one, two, three or more substituents, which may be the same or different, each replacing a hydrogen atom. Examples of substituents include but are not limited to halogen (e.g., F, Cl, Br, and I), hydroxyl, protected hydroxyl, amino, protected amino, carboxy, protected carboxy, cyan, methylsulfonylamino, alkoxy, alkyl, aryl, aralkyl, acyloxy, nitro, and lower haloalkyl.

An aryl group is a $C_{6-20}$ aromatic ring, wherein the ring is made of carbon atoms (e.g., $C_6$-$C_{14}$, $C_{6-10}$ aryl groups). Examples of haloalkyl include fluoromethyl, dichloromethyl, trifluoromethyl, 1,1-difluoroethyl, and 2,2-dibromoethyl.

An aralkyl group is a group containing 6-20 carbon atoms that has at least one aryl ring and at least one alkyl or alkylene chain connected to that ring. An example of an aralkyl group is a benzyl group.

A linking group is any divalent moiety used to link one compound to another. For example, a linking group may link a second compound to a compound of Formula I. An example of a linking group is ($C_1$-$C_{10}$) alkyloxy-($C_1$-$C_{10}$) alkyl.

Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure. Further examples and conditions are found in T. W. Greene, Protective Groups in Organic Chemistry, (1st ed., 1981, 2nd ed., 1991).

A person of skill will recognize that various ceragenin compounds described herein preserve certain stereochemical and electronic characteristics found in steroids. The term "single face," as used herein, refers to substituents on the fused sterol backbone having the same stereochemical orientation such that they project from one side of the molecule. For example, substituents bound at $R_3$, $R_7$ and $R_{12}$ of Formula I may be all 13-substituted or a-substituted. The configuration of the moieties $R_3$, $R_7$ and $R_{12}$ may be important for interaction with the cellular membrane.

Compounds include but are not limited to compounds having cationic groups (e.g., amine or guanidine groups) covalently attached to a sterol backbone or scaffold at any carbon position, e.g., cholic acid. In various embodiments, a group is covalently attached at anyone, or more, of positions $R_3$, $R_7$, and $R_{12}$ of the sterol backbone. In additional embodiments, a group is absent from anyone, or more, of positions $R_3$, $R_7$, and $R_{12}$ of the sterol backbone.

Other ring systems can also be used, e.g., 5-member fused rings. Compounds with backbones having a combination of 5- and 6-membered rings are also contemplated. Cationic functional groups (e.g., amine or guanidine groups) can be separated from the backbone by at least one, two, three, four or more atoms.

Ceragenins with hydrophobic substituents can be prepared using the techniques described in Applicant's U.S. Pat. No. 6,767,904, with the modification being using longer chain alkyls to form a substituent that is more hydrophobic. For example, instead of using an octyl amine to form the functional group at $R_{17}$ (Formula I where q=0, a corresponding longer chain amine can be used.

IV. Non-Covalent Incorporation of Ceragenins into a Hydrogel Polymer

Ceragenin compounds incorporated into the hydrogel polymer can be non covalently associated with the polymer. Upon contact with moisture, the ceragenin can leach or elute from the polymer. Ceragenins are generally soluble in water, and ceragenins can be associated with hydrogel polymers to control release rates. Selection of appropriate hydrogel polymer and ceragenin structures allows for an extended period of release of the ceragenin.

For example, the group extending from a heteroatom (e.g., N) on $R_{17}$ (Formula I) can be tailored to allow varied rates of elution from the hydrogel polymer. Exemplary groups include lipids, hydrophobic chains (e.g., aliphatic), hydrophilic (e.g., polyethyleneoxide), or any chain that interacts with the polymer is a way that allows modification of the rate of elution. Longer chain lengths will retain the ceragenin within the polymer matrix (in particular the hydrophobic domains). In one embodiment, the ceragenin compound may have a carbon chain of at least 9 carbons attached to the D ring of the sterol group (Formula I). For example, the carbon chain of at least 9 carbons may be attached to $R_{17}$ group of Formula I, or the $C_{24}$ carbon or other similar carbon of a sterol backbone.

The particular ceragenins incorporated into the hydrogel polymer may be soluble or partially soluble in aqueous solutions. Additionally, ceragenins when blended with the water and the appropriate surfactant can be handled in the form of gels, or emulsions. Block copolymers based on ethylene oxide and/or propylene oxide, in particular, Pluronic-type surfactants, are especially useful for this purpose. Pluronic is a product of BASF, a business with offices in Port Arthur, Tex., USA.

Ceragenin compounds can be incorporated into the hydrogel polymer at any suitable step during manufacture of a hydrogel material or product. For example, in an embodiment, a hydrogel can be brought into contact with a solution of ceragenins by immersion, spraying, printing, or coating, etc. In one embodiment, the solvent is a solvent that causes swelling of the hydrogel and the solvent and ceragenin are applied to the hydrogel in try form, thereby causing the hydrogel polymer to swell. Suitable swelling solvents include short chain alcohols such as ethanol, methanol, isopropyl alcohol, and the like. If desired, the solvent used to incorporate the ceragenin can be removed, for example, by evaporation. If necessary the hydrogel can be dried by utilizing forced hot air, oven drying, air at room temperature, microwave drying, or the use of heated drying drums, vacuum chambers, etc. In some manufacturing systems the normal air flow and temperature sufficiently dry the substrate without a discrete drying process.

Ceragenin compounds are known to be soluble in water. Alternatively, ceragenin compounds are also soluble in such materials as ethanol (and other alcohols), propylene glycol, glycerine, and polyols, or mixtures thereof with or without water can be used in incorporate ceragenin compounds into the hydrogel material. Furthermore ceragenins can be incorporated as gels, emulsions, suspensions, and in dry form.

In another embodiment ceragenin is incorporated into a hydrogel polymer during formation of the hydrogel. Hydrogel polymers can commonly be made from the polymerization of monomers. In these processes, the ceragenin can be included in the monomer blend during polymerization. The ceragenin in final polymer can be noncovalently incorporated into the polymer and will accordingly elute when contacted with a solvent such as water.

V. Elution

When the ceragenin compound is incorporated into the hydrogel material, the hydrophobicity/hydrophilicity of the hydrogel polymer and the ceragenin compound are selected to cause the ceragenin compound to non-covalently bond to the hydrogel polymer. The non-covalent bonding prevents the ceragenin compound from being released all at once in the presence of a solvent. Rather, the bonding allows the ceragenin compound to be released over time in the presence of a solvent.

The non-covalent bonding depends on the composition of both the hydrogel material and the ceragenin and therefore need to be selected together to produce the desired elution. The selection is typically carried out by selecting a particular hydrogel material having desired chemical and mechanical properties for a particular application. For example, if the hydrogel is coated on a medical device to be implanted in vascular tissue, the hydrogel is selected for compatibility with vascular tissue and blood. If the hydrogel is used to form a contact lens, the hydrogel is selected for its compatibility with the eye and the need to form the hydrogel in a shape that will correct vision. The hydrophobicity/hydrophilicity of the hydrogel material is therefore somewhat constrained by the particular application.

The ceragenin compound is selected to provide non-covalent bonding to the particular hydrogel. The ceragenin may be selected to have R groups that bond non-covalently the functional groups of the hydrogel. For example, a polyacrylate based hydrogel may have a certain percentage of hydrophobic groups and hydrophilic groups in the polymer matrix and the ceragenin compound may be selected to have a hydrophobic $R_{17}$ group that non-covalently bonds to the hydrophobic groups of the hydrogel to cause a relatively consistent elution over a period of days or weeks.

In some cases, the solvent may also influence elution. In one embodiment, the solvent is water. The amount of solvent in the hydrogel material may be greater than that of the hydrogel polymer. In one embodiment, the hydrogel material is at least 50%, 90%, or 99% by weight solvent. In some embodiments, the solvent may be saline.

In one embodiment, the hydrogel polymer and the ceragenin compound are selected to yield non-covalent bonding that provides a release rate of 0.1-100 µg/ml, 0.5-50 µg/ml, or 1-10 µg/ml at three days, one week, or one month in water or saline. In one embodiment, the foregoing elution rate remains within the foregoing ranges for at least 3 days, one week, or one month. These elution rates are achieved in part by the non-covalent bonding that prevents rapid release of the compound, which results in more compound being available at a later date.

As mentioned above, it has been surprisingly found that non-covalently bound ceragenins in hydrogels selectively elute in the presence of microbes. This is a surprising and unexpected result that makes the use of hydrogel-ceragenin compounds particularly advantageous as compared to other materials, such as ceragenins covalently bonded to the surface of a polymer.

In one embodiment, the ceragenin compound is selected according to its hydrophobicity. Desired hydrophobicities for eluting from polymers with hydrophobic groups are compounds with a CLogP value greater than 6.5, 7.5, 8.5 or in some cases even greater than 10. The CLogP value of various compounds is provided with the compounds in FIG. 1.

Those skilled in the art will recognize that the selection of the particular hydrogel and ceragenin compound will depend on the particular application and the appropriate selection can be made by one of skill in the art using the teachings and examples provided herein.

VI. Medical Devices and Coatings

Figure 2:
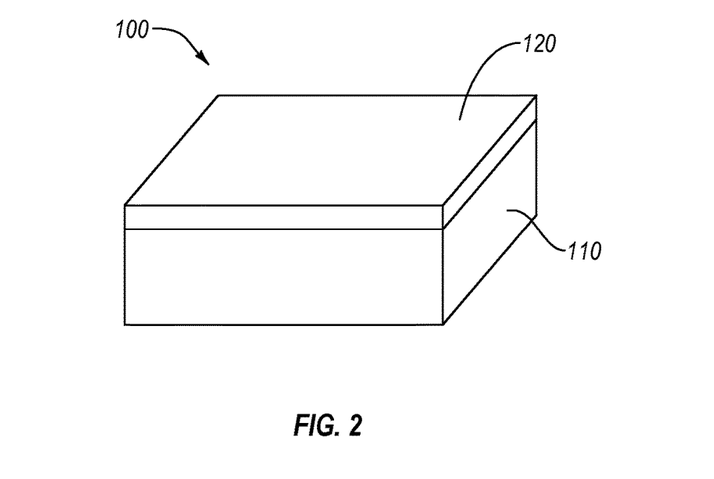
FIG. 2 is a schematic representation of a substrate with a hydrogel coating.

The hydrogels described herein may be used in various applications, including, but not limited to, medical devices, coatings, bandages, implants, tissue scaffolding, and the like. FIG. 2 is a schematic representation of a medical device 100 that includes a substrate 110 and a hydrogel coating 120.

The substrate 110 may be made of any material suitable for supporting and/or adhering to a hydrogel material. The substrate can be polymeric, metallic, an alloy, inorganic, and/or organic. In one embodiment, the substrate is a biocompatible or bioabsorbable material. Suitable biocompatible metallic materials include, but are not limited to, stainless steel, tantalum, titanium alloys (including nitinol), and cobalt alloys (including cobalt-chromium-nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, ε-caprolactone, and the like, and combinations of these)

The thickness of the substrate will depend on the device and the material but may be 0.1, 1.0, 10 mm or greater and/or 100, 10, or 1 mm or less and/or within a range thereof.

The thickness of hydrogel coating 120 is generally less than the thickness of substrate 110. Hydrogel coating 120 may have a thickness of 0.01, 0.1, 1.0, or 10 mm or greater and 100, 10, 1.0, or 0.1 mm or less or within a range thereof.

The coating 120 can be continuous or non-continuous. The coating may be applied to the substrate using techniques such as dip coating, spin coating, or the like.

Examples of medical devices that can be formed from a hydrogel containing ceragenin eluting compounds or can have such a hydrogel coated thereon include but are not limited to bone implants, bone pins, bone screws, tissue grafts, airway devices such as endotracheal tubes, implantable devices such as coronary stents, peripheral stents, catheters, arterio-venous grafts, by-pass grafts, pacemaker and defibrillator leads, anastomotic clips, arterial closure devices, patent foramen ovale closure devices, and drug delivery balloons. The hydrogel may be coated on or form any portion of the structures of such devices and is preferably on an outer surface and more preferably on an out service that contacts tissue or a tissue air interface (when the device is implanted).

VII. Stabilization of Ceragenins by pH

In one embodiment a ceragenin compound can have hydrolysable linkages that attach the cationic groups to the sterol group (e.g., ester bonds). Hydrolysis of these linkages inactivates the ceragenin. To make the ceragenin stable, an acid can be added to achieve a pH less than 6, 5.5, 5, or 4.5 and optionally greater than 2, 2.5, or 3 or a range thereof. Stability before use is important to give a desired shelf life and instability during and after use can be desirable to prevent long term accumulation of ceragenins in biological systems.

As discussed above, it may be advantageous to adjust the degree of neutralization of the hydrogel polymer to improve the stability of the ceragenin. The degree of neutralization of the hydrogel polymer can be adjusted during its manufacturing process, or subsequently. Alternatively, the ceragenin can be suspended or dissolved in an acidic solution; and when the ceragenin suspension or solution is added to the hydrogel polymer the degree of neutralization of the hydrogel would thereby be adjusted.

VIII. Examples

To better understand the mechanism by which ceragenin compounds can be eluted from a hydrogel to prevent bacterial colonization, we determined the rate at which CSA-138 elutes from a hydrogel suitable for use in contact lenses. To quantify the amount of ceragenin eluting from the hydrogel, we used LC/MS using a mass-labeled internal standard. However, this method only gave detection limits of about 2 µg/ml, and we were able to effectively kill bacteria at constant elution rates below the detection limit. For example, the elution fell below detection limits within five days of elution from lenses in which CSA-138 had been incorporated at 1%, yet the ceragenins appeared to still be providing suitable kill rates.

To decrease the detection limit for CSA-138, we prepared a radiolabeled version of CSA-138 (CSA-138T2), incorporated it into contact lenses, and quantified its elution from lenses using scintillation counting.

Example 1

Lenses containing 1% CSA-138 were stored in 0.5 mL phosphate buffered saline (PBS) prior to testing. One set of lenses was autoclaved for 45 min before elution studies were performed. For elution studies, lenses were suspended in 2 ml aliquots of PBS, 10% TSB growth medium, 10% TSB growth medium containing $10^6$ CFU of *Staphylococcus aureus*, or 10% TSB growth medium containing $10^6$ CFU of *Pseudomonas aeruginosa*. Corresponding aliquots were exchanged every 24 h, including bacterial inocula. Samples were removed every 24 h and analyzed for the presence of CSA-138 using scintillation counting. A standard curve was generated to correlate counts per minute to concentration of CSA-138. All experiments were performed in triplicate.

Figure 3:
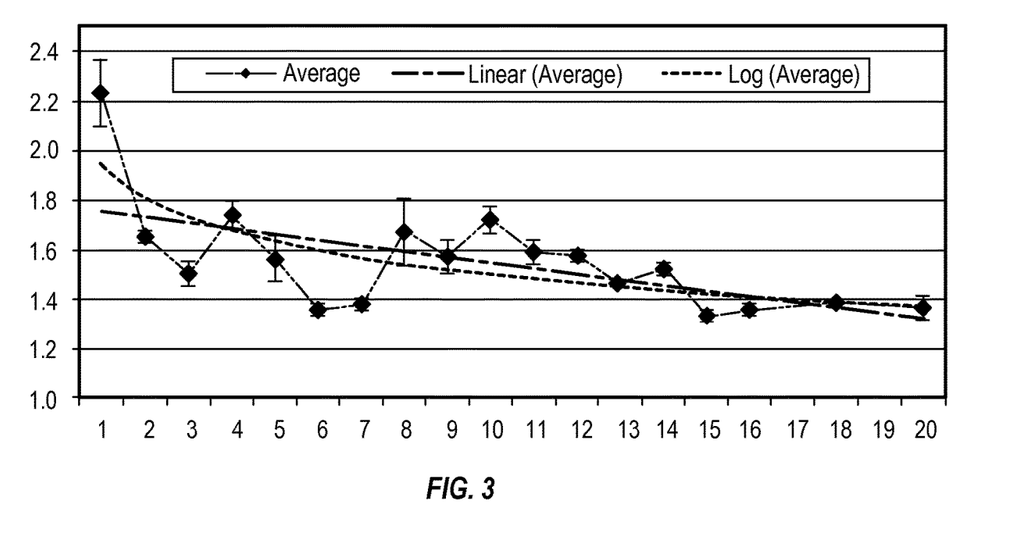
FIG. 3 is a graph showing elution of a ceragenin from a hydrogel in phosphate buffered saline.

Though some variations from day to day were observed, a recognizable trend was observed in the elution profile of lenses suspended in PBS (FIG. 3). As expected, the elution on the first day was relatively high (about 2.2 µg/ml). Over the course of following 19 days, daily elution changed from approximately 1.6 to 1.4 µg/ml per day.

Figure 4:
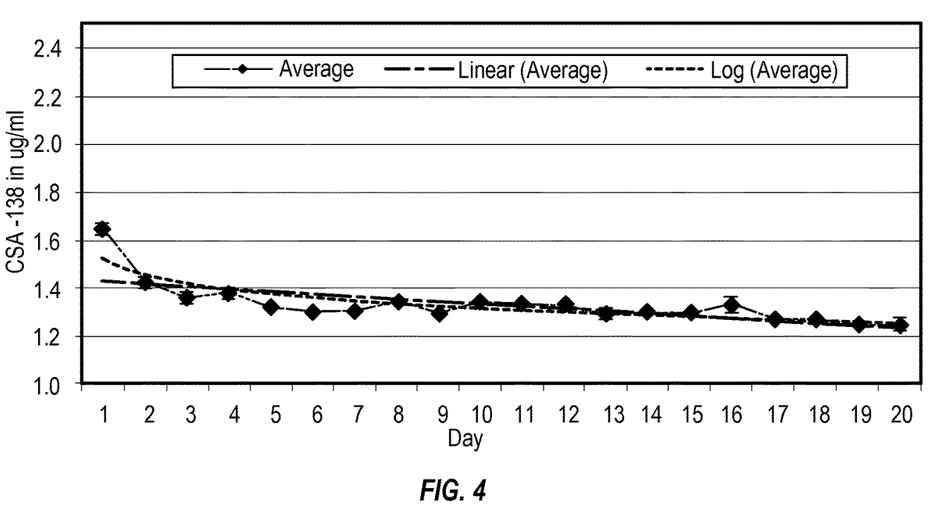
FIG. 4 is a graph showing elution of a ceragenin from a hydrogel following autoclaving.

A comparable elution profile was observed with lenses that were autoclaved prior to the start of the study, except that the initial amount of material that eluted decreased somewhat (FIG. 4). This decrease in elution is likely due to enhanced elution into the storage solution during the autoclaving process. Over the course of the study (from day 2 to 20), the amount of CSA-138 that eluted changed from approximately 1.4 to 1.2 µg/ml per day.

It was anticipated that an increase in the osmolality of an aqueous solution would decrease the solubility of CSA-13 and slow elution. We determined the elution profile in 10% TSB in PBS, and as expected elution decreased (FIG. 5) to match that seen with lenses that had been autoclaved.

Figure 6:
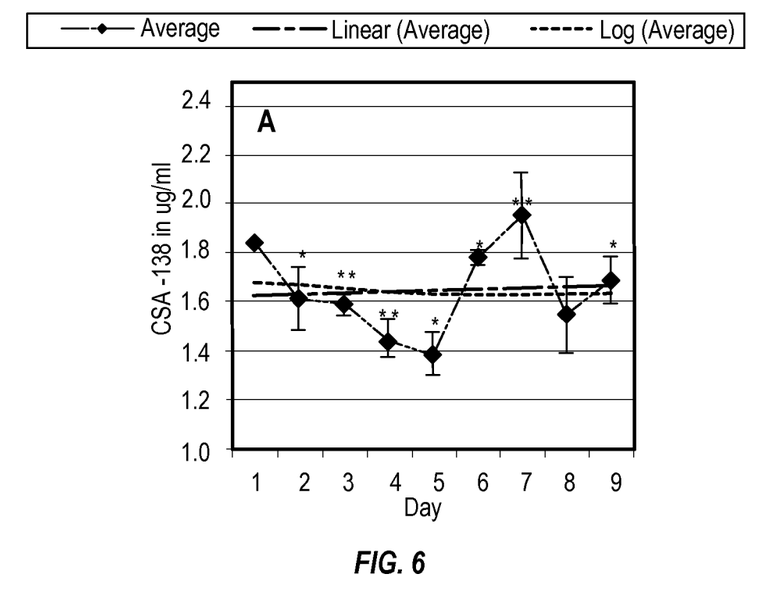
FIG. 6 is a graph showing elution of a ceragenin from a hydrogel in buffer and $10^6$ CFU of *S. aureus*.
Figure 7:
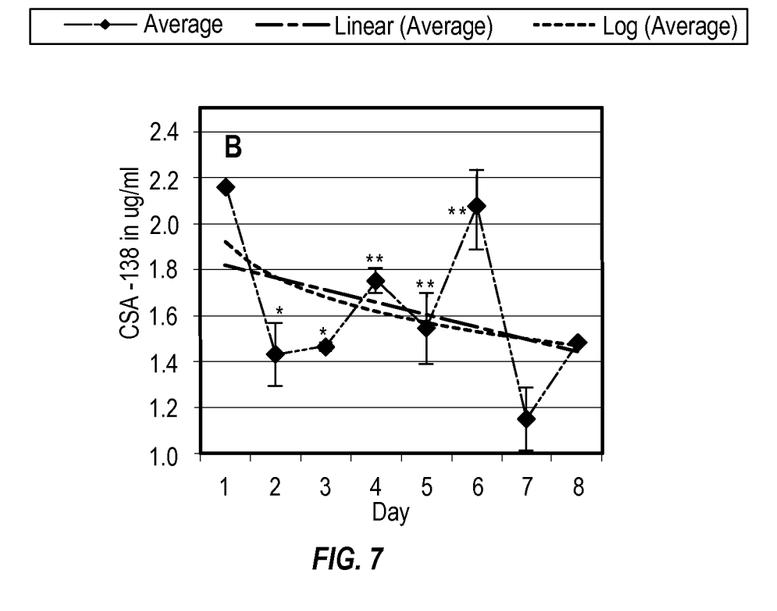
FIG. 7 is a graph showing elution of a ceragenin from a hydrogel in buffer and $10^6$ CFU of *P. aeruginosa*.

Because kill rates appeared to be happening at such low concentrations, we hypothesized that the presence of bacteria was influencing the elution of CSA-138 from lenses. To test this hypothesis, lenses were incubated with *S. aureus* or *P. aeruginosa* and elution was monitored. These experiments were performed for nine and eight days, respectively. Elution of CSA-138 fluctuated substantially and to a much greater extent than outside of the presence of bacteria (FIGS. 6 and 7). Because of these variations, the experiments were shortened relative to elution experiments without bacteria. Though there was substantial variation in the elution in the presence of bacteria, it was possible to determine the significance of the differences in elution comparing samples with and without bacteria. After the first day, differences gave a p value of 0.05 and for many of the days, the p value was below 0.01. These results argue that bacteria impact elution of CSA-138 from lenses.

The MIC values of CSA-138 for *S. aureus* and for *P. aeruginosa* are 0.5 and 1.0 µg/ml, respectively. The elution of CSA-138 from lenses gives concentrations that are just able to eliminate the inocula introduced. Autoclaving the lenses, increasing the osmolality in the surrounding solution, and the presence of bacteria impact the elution profile modestly.

Figure 5:
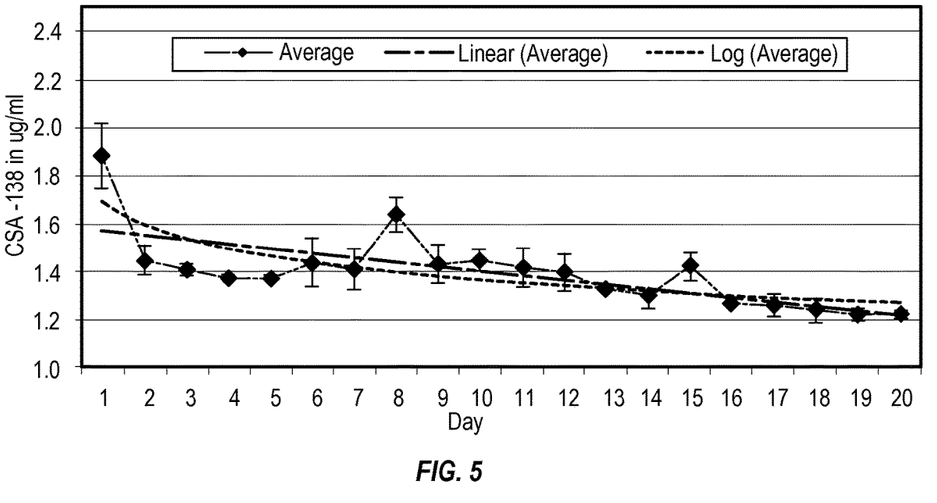
FIG. 5 is a graph showing elution of a ceragenin from a hydrogel in phosphate buffered saline and tryptic soy broth.

If one takes the elution profile given in FIG. 5 and extends the trend until elution of CSA-138 drops below 1 µg/ml, this would require about 40 days (elution decreases from 1.4 to 1.2 µg/ml per day between days two and 20; a decrease from 1.2 to 1.0 µg/ml per day would be expected to require another 19 days). Thus, it would be expected that elution of CSA-138 would be sufficient to eliminate reasonable inocula of bacteria for as many as 40 days. As noted in a previous report, elution of CSA-138 from lenses prevents colonization by *S. aureus* for 30 consecutive days and by *P. aeruginosa* for 19 days. These studies are performed with relatively high inocula ($10^6$ CFU), and it is anticipated that CSA-138 eluting after 30 days would be sufficient to eliminate smaller inocula.

Optimization of the structure of CSA-138 has yielded a potent antimicrobial agent that associates with contact lens material and elutes at the concentration necessary to eliminate substantial inocula of Gram-positive and -negative bacteria. Considering the number of bacteria to which lenses are typically exposed, it is likely that lower concentrations of CSA-138 could be used while continuing to prevent bacterial growth on lenses.

For purposes of this invention, "physiological conditions" are aqueous conditions where the pH, temperature, and salt concentrations are generally suitable for sustaining life (e.g., for many, but not all devices, physiological conditions is often a pH near 7, temperatures near 37° C., and salt concentration near 150 mM).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A ceragenin eluting hydrogel material, comprising
a hydrogel polymer selected from the group consisting of polyvinyl alcohol, sodium polyacrylate, acrylate polymers, poly(2-acrylamido-2-methyl-1-propanesulfonic acid (polyAMPS), polyvinylpyrrolidone, polyacrylamide, silicone, agarose, methylcellulose, hyaluronan, hydrolyzed polyacrylicnitrile, cross-linked polymers based on hydrophilic derivatives of acrylic or methacrylic acid, and cross-linked polymers based on hydrophilic vinylic monomers, and combinations of the foregoing;
at least 50% by weight water absorbed into the hydrogel polymer; and
a ceragenin compound mixed with the hydrogel polymer and non-covalently bonded thereto, the ceragenin compound comprising a hydrophobic sterol backbone, a hydrophobic substituent joined to the sterol backbone, and a plurality of hydrophilic cationic groups, wherein the ceragenin compound is anti-bacterial, anti-viral, or anti-fungal, wherein the ceragenin eluting hydrogel material forms at least an outer surface of a medical device, contact lens, or other substrate having a fixed shape and structure,
wherein hydrophobic/hydrophilic interactions between the ceragenin compound and the hydrogel polymer control the rate of elution of the ceragenin compound from the hydrogel polymer when the outer surface of the medical device, contact lens, or other substrate is exposed to water and/or microbes so that the ceragenin compound controllably elutes from the hydrogel material in excess water at a rate of 0.1-100 µg/ml at 3 days, one week, or one month and/or over a period of 3 days, one week and/or one month,
wherein at last a portion of the hydrogel material is coated on a medical device, contact lens, or other substrate of fixed shape and structure.

2. A ceragenin eluting hydrogel material as in claim 1, wherein the ceragenin compound elutes from the hydrogel material in excess water at a rate of 1-10 µg/ml at 3 days, one week, or one month and/or over a period of 3 days, one week and/or one month.

3. A ceragenin eluting hydrogel material as in claim 1, wherein the hydrogel material comprises at least 90% by weight water absorbed into the hydrogel polymer.

4. A ceragenin eluting hydrogel material as in claim 1, wherein the water is a saline water.

5. A ceragenin eluting hydrogel material as in claim 1, wherein the hydrogel polymer includes polyvinyl alcohol, sodium polyacrylate, an acrylate polymer, polyethylene oxide, polyAMPS, polyvinylpyrrolidone, polyacrylamide, silicone, agarose, methylcellulose, hyaluronan, or a combination thereof.

6. A ceragenin eluting hydrogel material as in claim 1, wherein the hydrophobic substituent includes a carbon chain of at least 9 carbons.

7. A ceragenin eluting hydrogel material as in claim 1, having a structure as in Formula I:

Formula I wherein,
$q=0$ and $p=1$;
$R_3$, $R_7$, and $R_{12}$ independently include a cationic group; and
$R_{17}$ is a hydrophobic substituent comprising one or more heteroatoms selected from O or N and at least one carbon chain of at least 9 carbons extending from the heteroatom.

8. A ceragenin eluting hydrogel material as in claim 1, wherein a portion of the hydrogel material is formed into a structure of the medical device, contact lens, or other substrate of fixed shape and structure.

9. A ceragenin eluting hydrogel material as in claim 1, wherein the medical device is selected from the group consisting of bone implant, bone pin, bone screw, tissue graft, endotracheal tube, coronary stent, peripheral stent, catheter, arterio-venous graft, by-pass graft, pacemaker or defibrillator lead, anastomotic clip, arterial closure device, patent foramen ovale closure device, and drug delivery balloon.

10. A ceragenin eluting hydrogel material as in claim 1, wherein the type and concentration of the ceragenin compound is selected to provide a minimum inhibition concentration sufficient to inhibit the growth of Staphylococcus aureus type methicillin-resistant Staphylococcus aureus or vancomycin-resistant Staphylococcus aureus under physiological conditions.

11. The ceragenin eluting hydrogel material of claim 10, wherein the hydrogel material comprises silicone.

12. A ceragenin eluting hydrogel material, comprising:
a hydrogel polymer; and
a ceragenin compound incorporated into the hydrogel polymer and non-covalently bonded thereto, the ceragenin compound comprising a hydrophobic sterol backbone, a hydrophobic substituent joined to the sterol backbone, and a plurality of hydrophilic cationic groups, wherein the ceragenin compound is anti-bacterial, anti-viral, or anti-fungal,
wherein a first portion of the ceragenin eluting hydrogel material is formed into a shape and structure of a medical device, contact lens, or other substrate of fixed shape and structure,
wherein a second portion of the ceragenin eluting hydrogel material is coated on the medical device, contact lens, or other substrate of fixed shape and structure,
wherein hydrophobic/hydrophilic interactions between the ceragenin compound and the hydrogel polymer control the rate of elution of the ceragenin compound from the hydrogel polymer when the hydrogen material is exposed to water and/or microbes so that the ceragenin compound controllably elutes from the hydrogel material in excess water at a rate of 0.1-100 µg/ml at 3 days, one week, or one month and/or over a period of 3 days, one week and/or one month.

13. The ceragenin eluting hydrogel material of claim 12, wherein the ceragenin compound is selected from the group consisting of CSA-131, CSA-132, CSA-133, CSA-134, CSA-135, CSA-137, and CSA-138.

14. The ceragenin eluting hydrogel material as in claim 12, wherein the hydrogel material forms the shape and structure of a contact lens.

15. The ceragenin eluting hydrogel material of claim 1, wherein the ceragenin compound is selected from the group consisting of CSA-44, CSA-142, CSA-144, and CSA-146.

16. A ceragenin eluting hydrogel material forming a coating on an outer surface of a medical device, contact lens, or other substrate of fixed shape and structure, the ceragenin eluting hydrogel material comprising a hydrogel polymer selected from the group consisting of polyvinyl alcohol, sodium polyacrylate, acrylate polymers, poly(2-acrylamido-2-methyl-1-propanesulfonic acid (polyAMPS), polyvinylpyrrolidone, polyacrylamide, silicone, agarose, methylcellulose, hyaluronan, hydrolyzed polyacrylicnitrile, cross-linked polymers based on hydrophilic derivatives of acrylic or methacrylic acid, cross-linked polymers based on hydrophilic vinylic monomers, and combinations of the foregoing; and a ceragenin compound mixed with the hydrogel polymer and non-covalently bonded thereto, the ceragenin compound comprising a hydrophobic sterol backbone, a hydrophobic substituent joined to the sterol backbone, and a plurality of hydrophilic cationic groups, wherein the ceragenin compound is both anti-bacterial and anti-fungal, wherein hydrophobic/hydrophilic interactions between the ceragenin compound and the hydrogel polymer control the rate of elution of the ceragenin compound from the hydrogel polymer when exposed to water and/or microbes so that the ceragenin compound controllably elutes from the hydrogel material in excess water at a rate of 0.1-100 µg/ml at 3 days, one week, or one month and/or over a period of 3 days, one week and/or one month.

17. The ceragenin eluting hydrogel material of claim 16, wherein the ceragenin compound is selected from the group consisting of CSA-44, CSA-131, CSA-132, CSA-133, CSA-134, CSA-135, CSA-136, CSA-137, CSA-138, CSA-139, CSA-142, CSA-144, and CSA-146.

18. The ceragenin eluting hydrogel material of claim 16, wherein the hydrogel polymer is selected from the group consisting of polyvinyl alcohol, sodium polyacrylate, acrylate polymers, polyAMPS, polyvinylpyrrolidone, polyacrylamide, silicone, agarose, hyaluronan, hydrolyzed polyacrylicnitrile, cross-linked polymers based on hydrophilic derivatives of acrylic or methacrylic acid, and cross-linked polymers based on hydrophilic vinylic monomers, and combinations of the foregoing.

19. The ceragenin eluting hydrogel material of claim 16, wherein the hydrogel material further comprises at least 50% by weight water absorbed into the hydrogel polymer.

* * * * *

UNITED STATES PATENT AND TRADEMARK OFFICE
CERTIFICATE OF CORRECTION

PATENT NO. : 10,676,501 B2  
APPLICATION NO. : 13/554930  
DATED : June 9, 2020  
INVENTOR(S) : Paul B. Savage Page 1 of 1

It is certified that error appears in the above-identified patent and that said Letters Patent is hereby corrected as shown below:

On the Title Page

Item (56), References Cited, Other Publications, add –Bucki et al. (Salivary mucins inhibit antibacterial activity of the cathelicidin-derived LL-37 peptide but not the cationic steroid CSA-13, Journal of Antimicrobial Chemotherapy (2008) 62:329-335), 7 pages.–

In the Specification

Column 1
Line 20, change "compound" to –compounds–

Column 2
Line 19, change "and surprising" to –and a surprising–
Line 46, change "compound" to –compounds–

Column 5
Line 2, delete "four"

Column 5
Line 38, delete second instance of "a"
Line 50, change "CSA's" to –CSAs–

Column 8
Line 3, change "anyone" to –any one–
Line 44, change "to $R_{17}$" to –to the $R_{17}$–

Signed and Sealed this  
Twenty-seventh Day of October, 2020

Andrei Iancu  
*Director of the United States Patent and Trademark Office*